United States Patent
Davis et al.

(10) Patent No.: US 10,557,833 B2
(45) Date of Patent: Feb. 11, 2020

(54) METHOD FOR PRIORITIZING DATA PROCESSING OF A PLURALITY OF ULTRASONIC SCAN DATA FILES

(71) Applicant: VeriPhase, Inc., Birmingham, AL (US)

(72) Inventors: John Mark Davis, Hoover, AL (US); Archibald Leach Cobbs, Mountain Brook, AL (US); Charles Allan Hansen, Sterrett, AL (US); Nicholas James Bublitz, Chelsea, AL (US); Samuel Matthew Davis, Birmingham, AL (US)

(73) Assignee: VeriPhase, Inc., Birmingham, AL (US)

( * ) Notice: Subject to any disclaimer, the term of this patent is extended or adjusted under 35 U.S.C. 154(b) by 0 days.

(21) Appl. No.: 16/416,164

(22) Filed: May 18, 2019

(65) Prior Publication Data
US 2019/0271668 A1 Sep. 5, 2019

Related U.S. Application Data

(63) Continuation-in-part of application No. 16/402,715, filed on May 3, 2019, and a continuation-in-part of application No. 16/375,611, filed on Apr. 4, 2019, and a continuation-in-part of application No. 14/986,195, filed on Dec. 31, 2015, now Pat. No. 10,324,066.

(51) Int. Cl.
*G01N 29/44* (2006.01)

(52) U.S. Cl.
CPC ..... *G01N 29/44* (2013.01); *G01N 2291/0289* (2013.01); *G01N 2291/267* (2013.01)

(58) Field of Classification Search
CPC ........... G01N 29/44; G01N 29/4445; G01N 2291/044; G01N 2291/0234; G01N 2291/0289; G01N 2291/267–2677
See application file for complete search history.

(56) References Cited

U.S. PATENT DOCUMENTS

| | | | | |
|---|---|---|---|---|
| 4,967,381 A | * | 10/1990 | Lane | G05B 15/02 700/17 |
| 2005/0054921 A1 | * | 3/2005 | Katsman | G01S 7/003 600/437 |
| 2006/0288304 A1 | * | 12/2006 | Nomoto | G06F 16/168 715/781 |
| 2007/0032968 A1 | * | 2/2007 | Nakamura | G01H 1/003 702/56 |

(Continued)

FOREIGN PATENT DOCUMENTS

WO    WO 2016/153562    9/2016

*Primary Examiner* — Natalie Huls
(74) *Attorney, Agent, or Firm* — The Gache Law Firm, P.C.; Russell C. Gache

(57) ABSTRACT

A method is disclosed provide a method of collecting a group of scan data files and organizing those files for batch data processing to produce a weld indications table for each scan data file in a prioritized manner. The invention also provides a procedure for controlling the pre-processing of each file by extracting meta-data held in an ultrasonic data file and from such data determine whether the testing data is valid for review. A series of rules may be used by a selection engine to control a batch list of files for data processing and for review after data processing so that time by a weld inspector may be optimized for each construction project.

20 Claims, 5 Drawing Sheets

(56) References Cited

U.S. PATENT DOCUMENTS

| | | | |
|---|---|---|---|
| 2007/0157730 A1* | 7/2007 | Ochiai | F22B 37/003 |
| | | | 73/627 |
| 2008/0010293 A1* | 1/2008 | Zpevak | G06Q 10/06 |
| 2008/0021834 A1* | 1/2008 | Holla | G06F 21/602 |
| | | | 705/51 |
| 2014/0238136 A1* | 8/2014 | Ten Grotenhuis | |
| | | | G01N 29/0654 |
| | | | 73/592 |
| 2015/0127502 A1 | 5/2015 | Knepfle et al. | |
| 2016/0206283 A1* | 7/2016 | Ota | A61B 8/4245 |
| 2017/0169128 A1* | 6/2017 | Batchu Krishnaiahsetty | |
| | | | H04N 1/32122 |
| 2018/0011973 A1* | 1/2018 | Fish | G06F 21/35 |
| 2018/0031152 A1* | 2/2018 | Rajagopalan | B23K 37/003 |
| 2019/0026935 A1* | 1/2019 | Podziemski | G06T 15/08 |

\* cited by examiner

METHOD FOR PRIORITIZING DATA PROCESSING OF A PLURALITY OF ULTRASONIC SCAN DATA FILES

This application claims the benefit of filing priority under 35 U.S.C. § 119 and 37 C.F.R. § 1.78 of the co-pending U.S. non-provisional application Ser. No. 14/986,195 filed Dec. 31, 2015, for a System and Method for the Improved Analysis of Ultrasonic Weld Data, and of co-pending U.S. non-provisional application Ser. No. 16/375,611 Ultrasonic Weld Analysis for Orthotropic Steel Decking Systems in Bridges filed Apr. 4, 2019, and co-pending U.S. non-provisional application Ser. No. 16/402,715 filed May 3, 2019, for a Method for Checking for Consistency and Quality Compliance in an Ultrasonic Scanning Data File. All information disclosed in those prior pending nonprovisional applications is hereby incorporated by reference.

FIELD OF THE INVENTION

The present invention relates generally to batch processing of computer files. In greater particularity, the present invention relates to batch prioritization of data processing of scan data files created during the testing of materials using ultrasonic testing equipment.

BACKGROUND OF THE INVENTION

Ultrasonic testing (UT) is a family of non-destructive testing techniques based on the propagation of ultrasonic waves in the object or material tested. In most common UT applications, very short ultrasonic pulse-waves with center frequencies ranging from 0.1-15 MHz, and occasionally up to 50 MHz, are transmitted into materials to detect internal flaws or to characterize materials. A common example is ultrasonic thickness measurement, which tests the thickness of a targeted object to determine the thickness of the object. Pipeline walls are routinely measured in this manner from the exterior of the pipeline to check for internal laminations and wall loss (corrosion and erosion)

Ultrasonic testing is often performed on steel and other metals and alloys, though it can also be used on concrete, wood and composites, albeit with less resolution. It is used in many industries including steel and aluminum construction, metallurgy, manufacturing, aerospace, automotive and other transportation sectors.

In ultrasonic testing, an ultrasound transducer connected to a diagnostic machine is passed over the object being inspected. The transducer is typically separated from the test object by a "couplant" such as oil or water. Phased array ultrasonics (PA) is an advanced method of ultrasonic testing that has applications in medical imaging and industrial nondestructive testing. Common industrial applications are noninvasive examination of manufactured materials such as welds joining large sections of pipes or steel decking for bridges.

Ultrasonic testers are typically separated into two classes of devices. Single-element (non-phased array) probes, known technically as monolithic probes, emit a beam in a fixed direction. To test or interrogate a large volume of material, a single-element probe must be physically scanned (moved or turned) to pass or traverse the beam through the area of interest. In contrast, multi-element (phased array) probes emit beams that can be focused and swept electronically without moving the probe. The beam is controllable because a phased array probe is made up of multiple small elements, each of which can be pulsed individually at a computer-calculated timing. The term "phased" refers to the timing, and the term "array" refers to the multiple elements. Phased array ultrasonic testing or "PAUT" is based on principles of wave physics, which also have applications in fields such as optics and electromagnetic antennae.

In the non-destructive testing of material and welds, the phased array probe emits a series of beams to flood the weld with sound and a flaw can be seen or "read" on a display screen attached to the phased array ultrasonic tester, usually highlighting a weld "indication" or potential flaw as a colored indication on the instrument display screen.

There are two main methods of receiving the ultrasound waveform: reflection and attenuation. In reflection mode sometimes referred to as "pulse-echo" mode, the transducer performs both the sending and the receiving of the pulsed waves as the "sound" is reflected back to the device. Reflected ultrasound comes from an interface, such as the back wall of an object, geometry reflections, or other foreign objects or from an imperfection within the object such as a weld defect. The diagnostic machine displays these results in the form of a signal with an amplitude representing the intensity of the reflection and the distance, representing the arrival time of the reflection. In attenuation mode sometimes referred to as "through-transmission" mode, a transmitter sends ultrasound through one surface, and a separate receiver detects the amount that has reached it on another surface after traveling through the medium. Imperfections or other conditions in the space between the transmitter and receiver reduce the amount of sound transmitted, thus revealing their presence. However, as is known, couplants are needed to provide effective transfer of ultrasonic wave energy between the transducer probes and the objects being inspected to reduce or eliminate the attenuation from air to ensure enough ultrasonic energy is present inside the object so a useable ultrasonic response can be obtained.

For the testing of materials and in particular for the testing of welds, the pulse-echo method is preferred and various PAUT devices are offered in the non-destructive testing industry for such testing. For example, Olympus Scientific Solutions Americas Inc., (aka Olympus NDT) based in Waltham, Mass., offers a product under the name OmniScan/OmniPC which may be used to test steel structures for determining inspection compliance. Using such a product is often referred to as "scanning" a weld and such testing produces "scan data" representing the area tested which can be read back and reviewed at a time of choosing by an inspector. Such captured scan data can be saved in common data storage systems, such as cloud-based storage, and retrieved at any time for review using known PC based systems. Further, later and evolving systems can access such weld scan data and assist in the identification of potential weld defects by removing nominal or non-suspect scan data to lessen the amount of time required for an inspector to review the data and to focus attention on suspected areas that may represent a potential weld flaw.

A suitable procedure for taking scans, recording those scans, and then analyzing the scans to reduce the examination burden for the inspector is found in U.S. patent application Ser. No. 14/986,195, pages 7-22, and all referenced figures, all of which are hereby incorporated by reference. In association with standard ultrasonic weld analysis techniques, and using the procedure disclosed in the above referenced application for determining ultrasonic reflection amplitudes (i.e. "voxels"), weld seams may be non-destructively tested to determine code or procedural compliance. Further discussion regarding the use of a PAUT system, understanding the testing procedures for welds using such a system, the reading of a PAUT display, the reading of a display produced by an associated PC application to view testing data, and how to calculate the distances and dimensions provided by such a testing application shall not be provided as such information is either well understood or fully disclosed in the above referenced application, or not necessary for a complete and full understanding of the herein described invention.

However, such UT data processing (also referred to herein as UT data analyzer or a UT data analyzation) as described in the above referenced application, irrespective of the sophistication of a PAUT device used to capture the data, may be of little usefulness if the inspector has not correctly configured the system prior to or during testing of the targeted weld area, even if the scanning was done with automated motorized scanners. Phased array inspectors must be trained and certified in the use of PAUT systems, their settings and limitations, and well understand the materials being targeted by the PAUT device for scanning, and the operator must be vigilant to configure the testing device correctly in order to obtain valid scan results. If a device is incorrectly configured, the UT data processing will not assist the examiner and, worse, may delay the discovery of a flawed data file until that data file is well past data processing when access to the tested area may be difficult or impossible in an ongoing construction environment.

As will be understood, the arrangement, scheduling, and organization of testing of welds in a construction project are complicated in their own right, and the rescanning of a weld area to produce a valid scan data file may cause costly delays in a construction project, or even interfere with other scheduled processes causing cascading schedule delays. Moreover, an inspector may spend a great deal of time reviewing scan data only to discover during their data inspection that the captured data itself is flawed and not usable for their code or procedural compliance objectives, sometimes causing confusion as to the source of the data capture flaw causing even more lost time to determine the source of the scanning error. Hence, the incorrect configuration of a testing device by a PAUT inspector can cause confusion and cost in a construction project.

Responsive to this need, the inventors have discovered a method for checking scan data files produced per the above described procedure for faults and inconsistencies. A series of tests for setup and configuration inconsistencies, and for quality testing of the data file, has been developed so that further data processing per the above procedure is not undertaken and wasted on a non-compliant data file. The process is a method of extracting meta-data held in an ultrasonic data file and from such data determine whether the testing data is valid for review. A series of configuration parameters held in the scan data file are analyzed for inconsistencies and a select set of parameters are reviewed for compliance with indications given. Additional qualitative tests may be implemented on the scan test file and results provided as guidance to the inspector as to whether continued review of the scan data file is worthwhile. The testing set is minimized so that a small core of tests can discern with a high level of probability whether the scan file is flawed and unsuitable for further data processing. A suitable process developed by the inventors may be found in U.S. patent application Ser. No. 16/402,715 filed May 3, 2019, for a Method for Checking for Consistency and Quality Compliance in an Ultrasonic Scanning Data File, pages 7-20, along with all referenced figures, all of which are hereby incorporated by reference.

One challenge created by the above described data processing and pre-testing procedures is that inspectors may wish to prioritize which files are to be processed and tested, so that they can prioritize the review of such data files in a manner that best fits the priorities of the construction project. For example, some inspection areas may have a higher priority due to construction schedules, and the inspection certification may be stopping the continuation of construction of certain parts of the project, thereby reducing the release of funding for the whole project. Alternatively, as may be understood, certain problems during welding operations may be noticed for certain sections of a construction project, and a construction manager may wish for such potentially problematic welds to be inspected before other pending weld inspections, even if those welds were scanned well after other welds were scanned. Since the above described data processing and pre-testing methods are new and not previously known in the industry, the automated processing and the control of such processing will now cause the availability of scan data files to become more rapidly available for an inspector's review, and an automated batch processing procedure, under priority control, is needed so that scan data files having a higher priority may be processed ahead of other scan data files.

Therefore, what is needed is a method for batching the processing of scan data files for consistency control and for data processing, and further a method for controlling the priority of such batch processing so that an inspector's time may be focused on reviewing indications data files in a controlled and prioritized manner.

SUMMARY OF THE INVENTION

It is the object of the present invention to provide a method of collecting a group of scan data files and organizing those files for batch data processing to produce an indication table for each scan data file in a prioritized manner. The present invention also provides a procedure for controlling the pre-processing of each file by extracting meta-data held in an ultrasonic data file and from such data determine whether the testing data is valid for review, thereby providing a method to exclude a data file from batch processing if the data is unreliable. A series of rules may be used by a selection engine to control a batch list of files for data processing and for review after data processing so that time by an inspector may be optimized for each project in accordance with the project priorities.

Other features and objects and advantages of the present invention will become apparent from a reading of the following description as well as a study of the appended drawings.

BRIEF DESCRIPTION OF THE DRAWINGS

A method incorporating the features of the invention is depicted in the attached drawings which form a portion of the disclosure and wherein.

DESCRIPTION OF THE PREFERRED EMBODIMENTS

Figure 1:
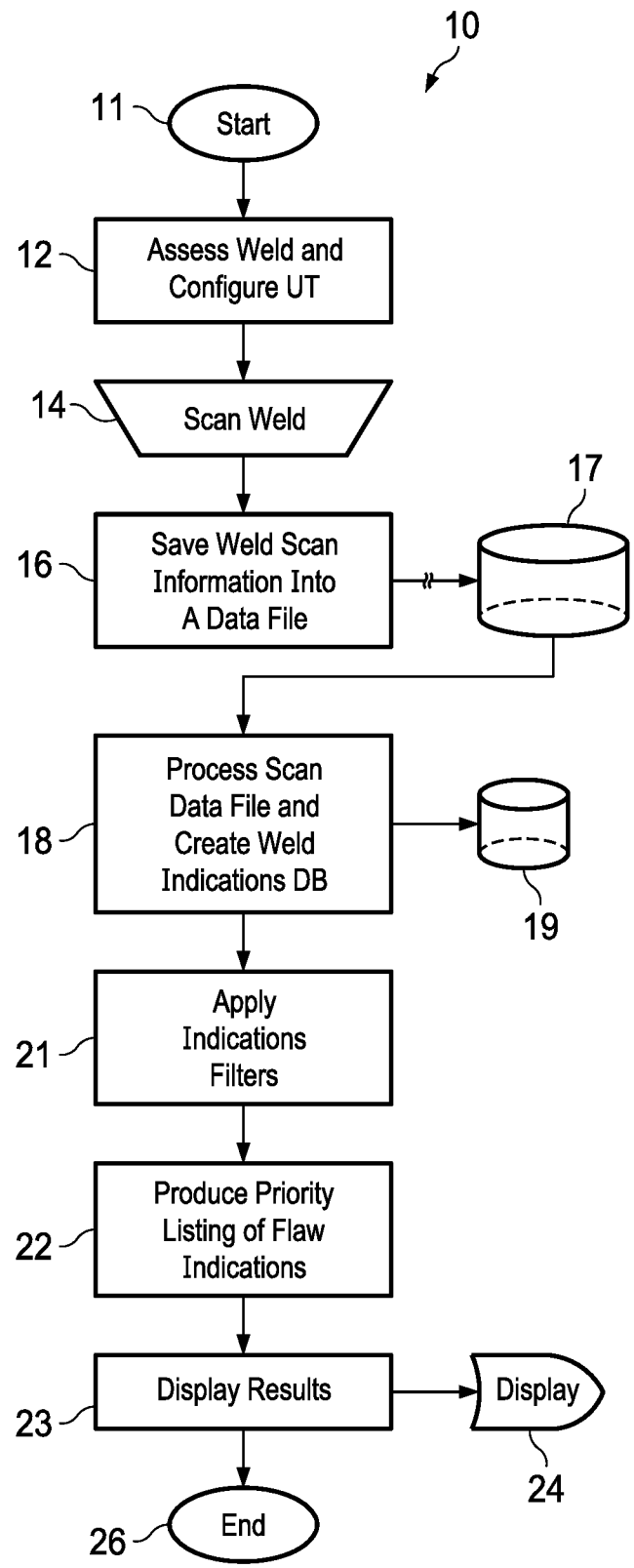
FIG. 1 a flow diagram showing the steps in collecting and data processing of scan data on a weld and the production of a listing of weld indications.

Referring to the drawings for a better understanding of the function and structure of the invention, FIG. 1 shows a method for collecting weld scanning data and the saving of such data into a scan data file for further analysis as disclosed in the above referenced U.S. patent application Ser. No. 14/986,195. As shown, system 10 shows a system that reduces the number of weld scan indications that an inspector must review in order to more efficiently produce a report meeting applicable welding examination codes and requirements, such as those published by ASME, AWS, or other organizations. The system 10 is a standard software application that may run on a standard Windows™ operating system, such as for example Windows 7 or Windows 10 sold by Microsoft Corporation, running on a standard PC configuration. The system may also be incorporated as a module directly into existing testing and/or scan analysis software.

Initially, an inspector assesses a weld situation and then configures their PAUT equipment for a scan, including the positioning of the UT probe 12 adjacent to a target weld. The weld is scanned by the inspector 14 and a data file recording the weld scan data saved 16. The data may be saved locally on the UT device, transferred to a connected drive storage 17, or uploaded to a network drive via Wi-Fi or other data connection, depending upon the size of the data file. The scan file is then processed 18 by extracting all data cuboids that include potential weld flaw indications, essentially extracting all cuboids that have amplitudes greater than 0, and then creates a file recording those indications and saves it in a local, fast access storage location 19. Further processing occurs on the indications file by applying a series of filters 21 that ranks and categorizes the indications into a usable form. In particular, a ranked list of indications is created in a table based on a ranking value for each indication which consists of multiple data cuboids. That priority listing of indications is then produced 22 and displayed 23 for the inspector's analysis at a place and time of their choosing.

The process shown in 10, referred to hereinafter as a UT data analyzer typically removes over 95 percent of the non-relevant data stored in a scan data file, and presents a focused list of only a fraction of the overall indications held by a scan data file, without degrading an inspector's ability to properly review the scan data in accordance with applicable code or procedural requirements.

However, in process 10 an assumption is made by the inspector reviewing the scan data file created in step 16 that the integrity of the data is consistent with acceptable testing practices in the weld scanning industry, and that such data meets minimum standards of weld practice analysis. Obviously, that may not be the case, so a system 30 is shown in FIG. 2 that can determine whether those minimum standards are met prior to the initiation of processing step 18.

Figure 2:
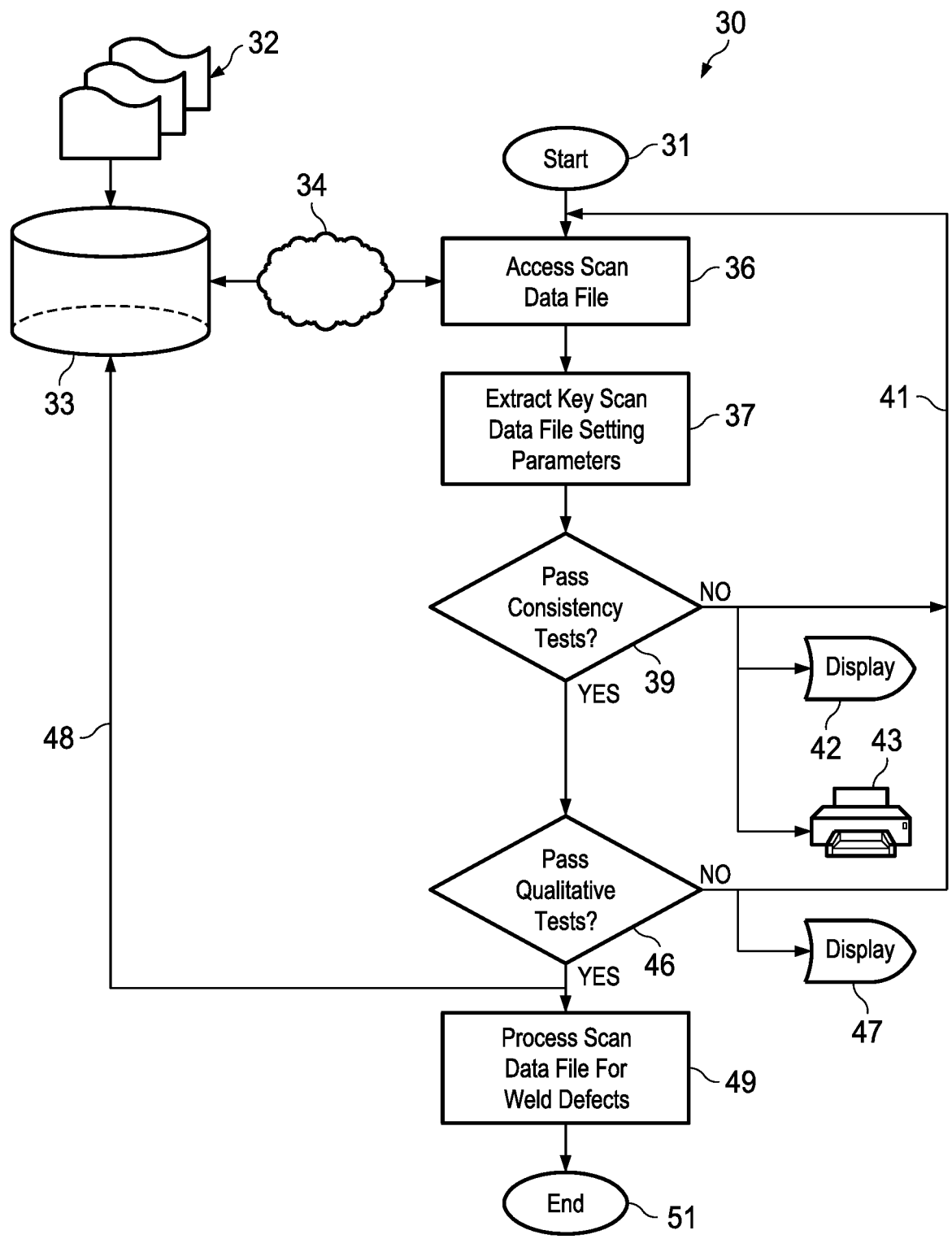
FIG. 2 is a flow diagram of steps to verify the integrity and validity of a scan data file by applying a set of consistency and quality tests, and from which a determination may be made as to its suitability for data processing for weld defects.

The system 30 in FIG. 2 is a software application held as an executable that may be initiated to pre-analyze a scan data file prior to further data processing. When invoked, the application reads the relevant configuration parameters from the data file. It then performs an analysis on the configuration parameters to verify that they, together in combination, represent a valid, correct and usable configuration. The results of this analysis are then presented to the human operator. The application may also work in conjunction with the UT data processing application described in FIG. 1, or work in a stand-alone configuration for processing a group of scan data files one after the other.

As shown in FIG. 2, a scan data file is accessed 36 from storage 33. Storage 33 may hold a plurality of scan data files 32 so that the system 30 may quickly process a group of scan data files in serial succession and report on each of those files in a processing order determined by the operators of the system. Such a configuration allows for the instant processing of files deposited in storage 33 or the delayed processing of select files to take advantage of scalable processing systems such as Amazon's AWS services. Irrespective, the order and timing of processing of each file may be done in a non-collocated manner so that cloud file storage 34 may be utilized for both processing and the saving of data files to a central cloud-based storage location as may be understood. Further discussion regarding the data processing of scan files 10 per FIG. 1 to produce an indications table, or the use of tests as a pre-processing step as shown in process 30 of FIG. 2 shall be omitted as such information is either fully disclosed in the above referenced applications, or not necessary for a complete and full understanding of the herein described invention.

Figure 3:
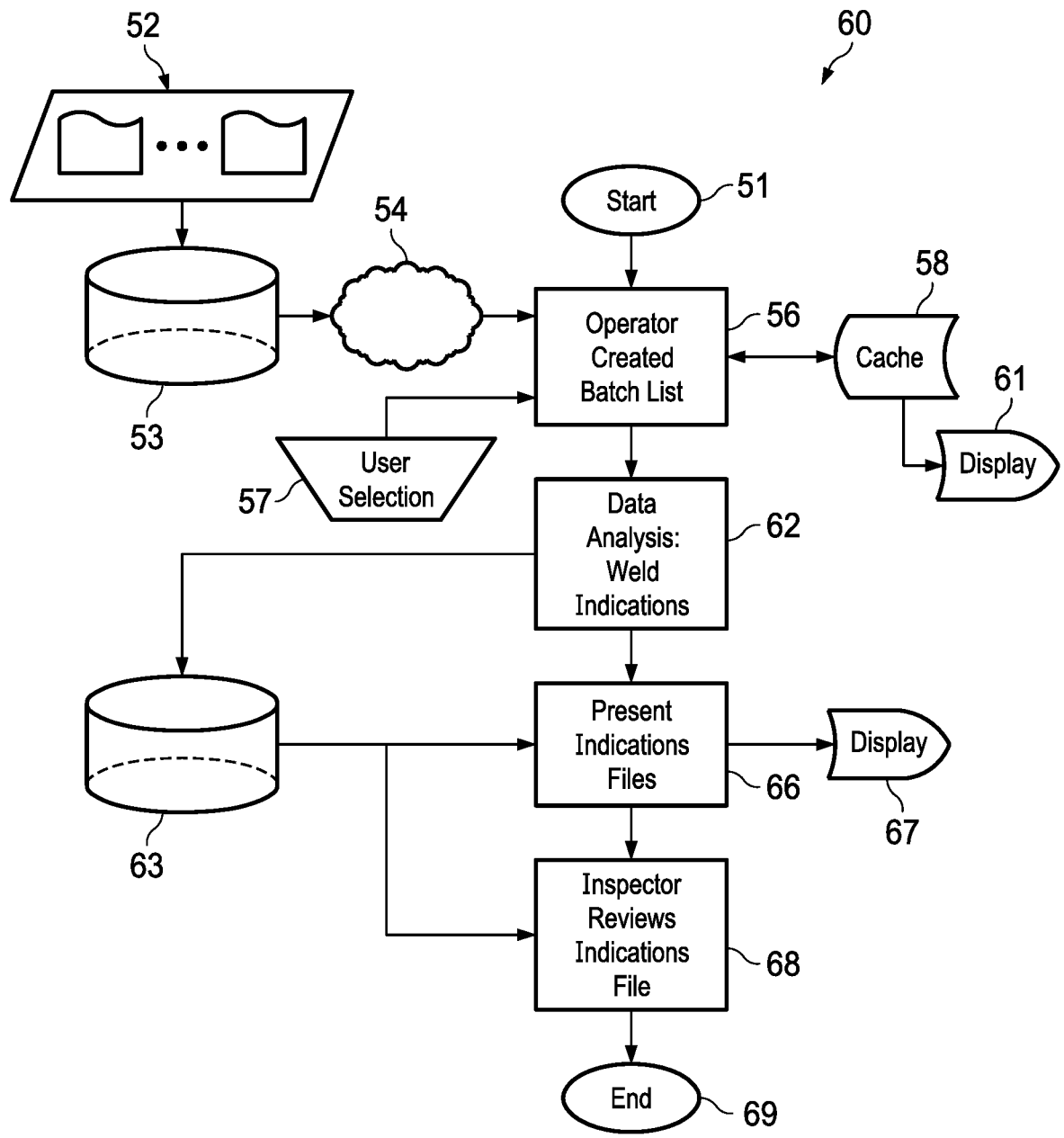
FIG. 3 is a flow diagram of the first embodiment of the invention where an operator determines a prioritized list of scan data files for data processing in accordance with the disclosed workings of the invention.

FIG. 3 shows a system and method 60 for ordering a group of scan data files for processing. The system 60 is a standard software application that may run on a standard Windows™ operating system, such as for example Windows 7 or Windows 10 sold by Microsoft Corporation, running on a standard PC configuration. The system 60 runs as a software application held as an executable that may be initiated from a standard windows interface to allow the listing, selection, and designation movements of files, as is known in standard human machine interface structures in windows and similar operating system environments.

A collection of scan data files 52 are held in computer data storage 53, such as cloud data storage accessible via an internet high-speed connection 54. A windowed interface is provided that allows an operator, such as a weld inspector, to select 57 a plurality of files stored in cloud storage 53 for processing, and order those files in a prioritized batch listing as desired by the operator 56. That prioritized listing 56 is cached in memory 58 and displayed to the operator 61 for confirmation. The system 60 then presents the prioritized listing of files to the data analysis application, such as described in FIG. 1 application 10, in a batch processing structure for data processing 62. As each scan data file is processed 62, the resulting indication files are saved in computer storage 63, such as local or cloud-based drive, and those processed indications files displayed 67 as each is completed 66. The weld inspector may then proceed to review each weld indications file in the order in which each is completed 68.

Figure 4:
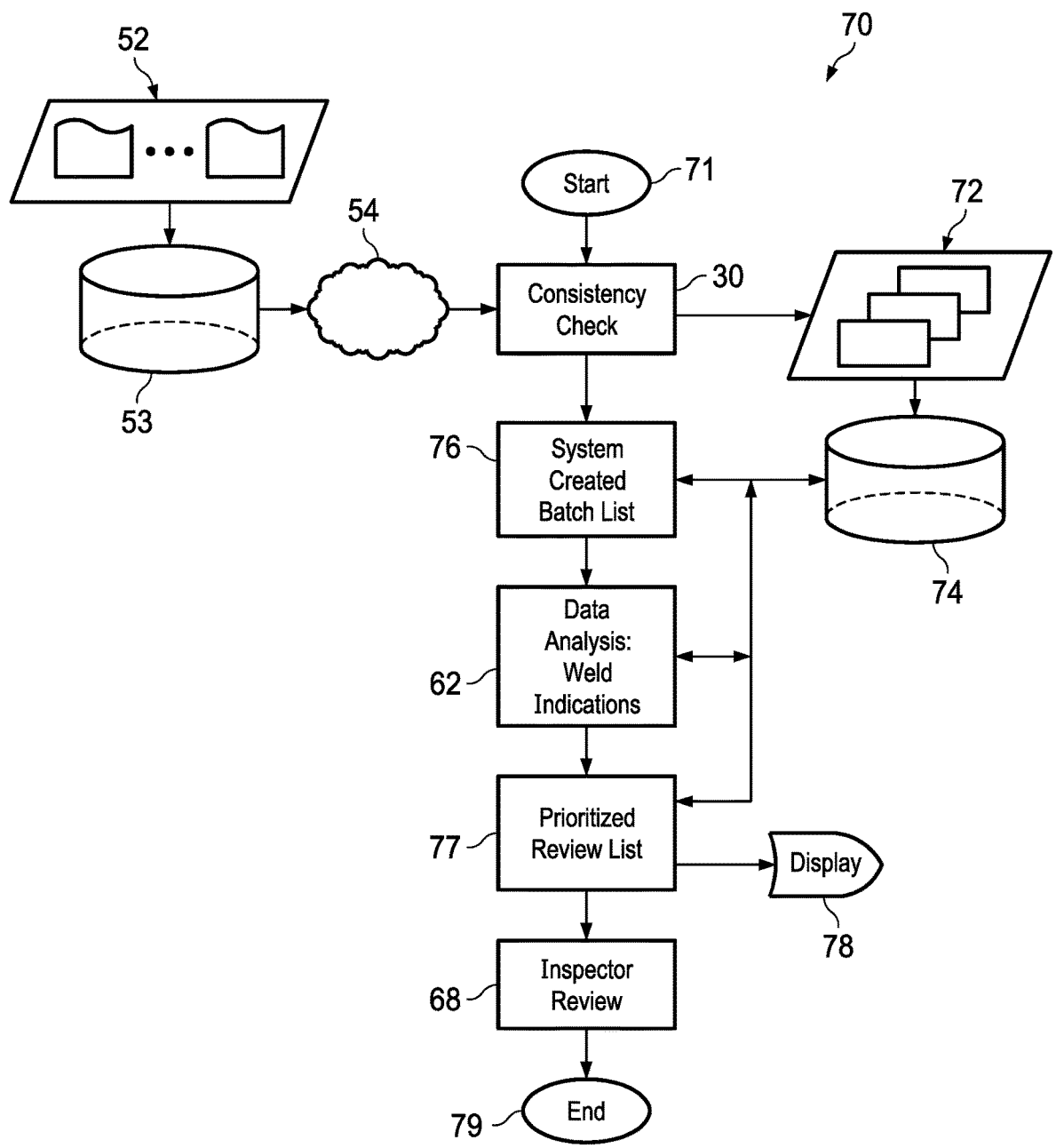
FIG. 4 is a flow diagram of a second embodiment of the invention where a file pre-check determines a prioritized list of scan data files for data processing in accordance with the disclosed workings of the invention; and, FIG. 5 is a flow diagram of a third embodiment of the invention where a file pre-check and a selection engine determines a prioritized list of scan data files for data processing and a prioritized list of indications files for review by a weld inspector, in accordance with the disclosed workings of the invention.

Referring to FIG. 4, a second embodiment is presented 70 in which a pre-check application directs the order of further data processing. In in the embodiment 60 of FIG. 3, scan data files are kept in storage 53 and accessed over a network, such as a high-speed internet connection 54. Each scan file as it becomes available in storage 53 is pre-processed using a consistency checking system 30 such as presented in FIG. 2 as application 30. If the scan data file passes the testing 30, each file is either passed on to a local storage location 74 or held in cloud storage 53 for later retrieval. If a scan data file does not pass testing step 30, a display signal is sent to an operator via an attached computer display to signify non-compliance and the file is excluded from the batch data processing list (step 76). At the direction of an operator, a report may also be printed recording the testing non-compliance. Depending upon the basis for the failure, the operator may take remedial action to correct a scan file configuration error by editing the file directly, and from which the file may be re-submitted for testing pursuant to step 30. If the data file cannot be corrected, further remediation action in the form of a second scanning of the weld may be necessary and a replacement scan data file processed in accordance with process 70. The storage 74 ends up either holding or designating a collection of files 72 suitable for data analysis 62 as described above. That file listing held in storage 74 automatically creates a priority list of files as a batched list of files 76, with such a list updated with more recently tested files as they become available after testing 30 as a dynamically updated listing. The order of the batched list is processed in data processing step 62 on a first in first out (FIFO) basis, and files holding weld indications after analysis step 62 being held in storage 74. Alternatively, a score may be produced during consistency check testing in step 30 and based on that scoring the files prioritized based on the test score for each file. In either case, a prioritized review list 77 is then presented 78 to a weld inspector 68 for review. The review list 77 is dynamically updated as files finish processing in step 62 and reviewed in a FIFO basis by the inspector 68. As per process 10, the inspector may produce a report associated with each scan data file displaying information characteristic of the processed scan data file.

Figure 5:
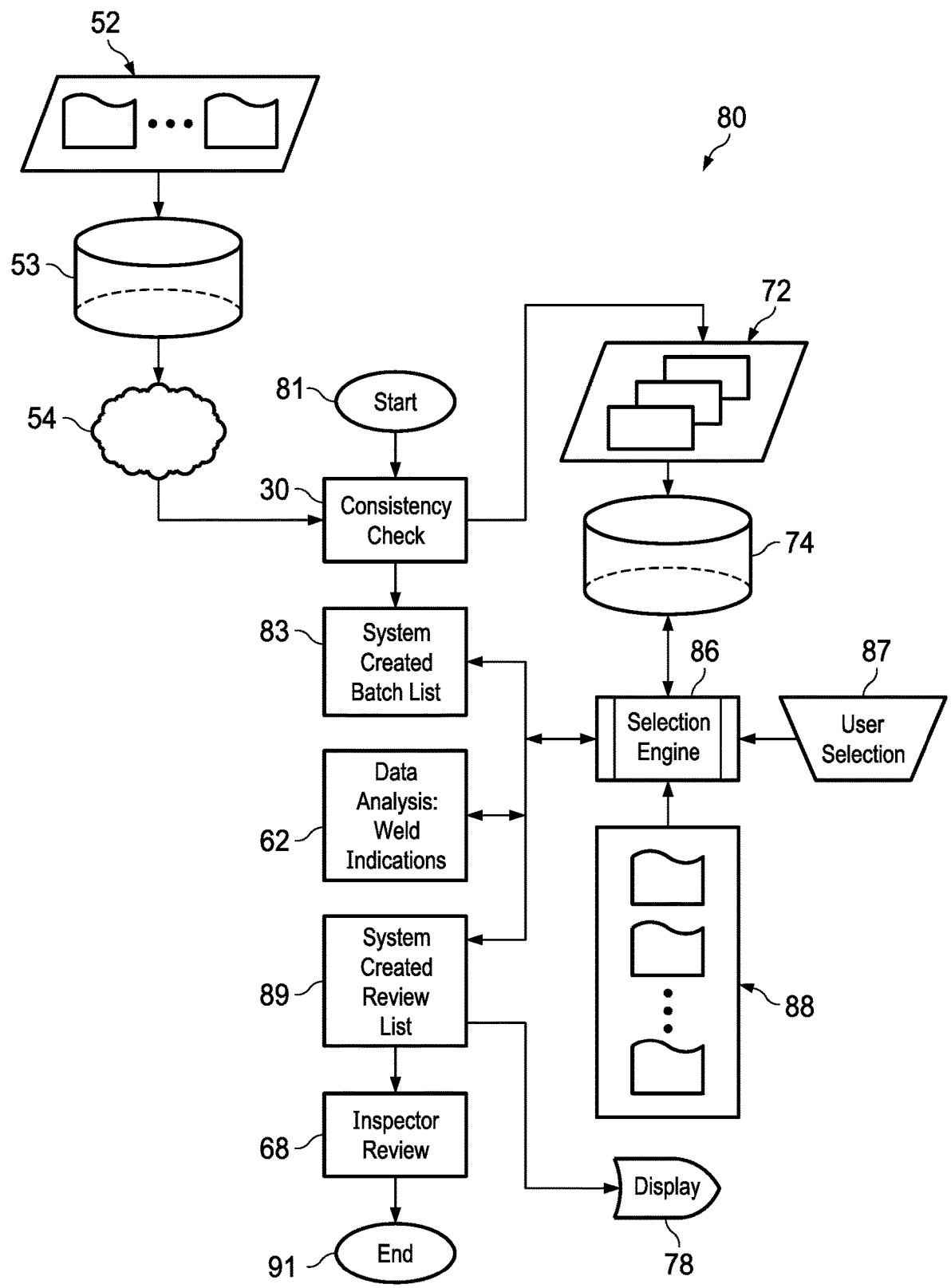

While system 70 presents a method to create a batched order of files based upon the FIFO passage of a consistency checking system 30, it may be desirable to process out of sequence each file and review each process file based on a set of rules or with user specified prioritization. FIG. 5 presents a third embodiment capturing that capability. The prior consistency pre-check step and cloud-based file access are the same as process 80. However, embodiment 80 includes a selection engine 86 to determine a batched list 83 for data analysis 62 to create a weld indications file. Selection engine 86 accepts rules input 88 to order batch list 83. Alternatively, based on user input 87 from a standard windows interface window, the selection engine may conform the selection to a FIFO prioritization list, dynamically updated, based on consistency check results as in embodiment 70 of FIG. 4. As a further alternative, selection input 87 may simply allow the operator to select certain files which will be kept at the top of the batch processing list in an order determined by the operator based on a ranked order presented in the selection window, or include a priority value, say from 1-100, that determines priority.

As each file is analyzed per step 62, selection engine 86 records the availability of each file as there are processed and dynamically ranks the files for review in a list 89 for the weld inspector to review 68 through display 78. As with the processing batch listing 83, rules 88 also impact the dynamic listing of indications files in step 89 by taking inputs from rules 88, and also accepting inputs from user selection 87 to selectively determine the review list based on an operator preference.

Rules 88 may be created in any manner typical for the batch processing of data files. For example, a file serial number may be assigned to each file as the file is created with each assigned file number including alpha-numerical character sequencing that corresponds to certain construction identification information. An operator may assign weighting rules for different scan data files based on such construction information, thereby allowing for prioritization of different scan data review based on construction timeline priorities. Alternatively, a characteristic of the actual scan data file may determine its priority per the rules list. For example, processing or transfer communications demands may at a priority and an operator may wish to prioritize processing of a file based on the size of the file, smaller files processed first, so that such resources may be optimized. Further, a time stamp may be added to the scan data file structure and the time stamp may determine priority, for example FIFO or LIFO (last in last out).

While I have shown my invention in one form, it will be obvious to those skilled in the art that it is not so limited but is susceptible of various changes and modifications without departing from the spirit thereof.

Having set forth the nature of the invention, what is claimed is:

1. A method for prioritizing data processing of a plurality of ultrasonic scan data files, comprising the steps of:
   a. responsive to the availability of a plurality of ultrasonic scan data files, presenting a list of scan data files available for data processing to an operator through a human machine interface on a computing device;
   b. conducting a plurality of tests upon said plurality of ultrasonic scan data files by retrieving configuration values in each said ultrasonic scan data file to determine the existence of configuration inconsistencies in said data file based upon one or more predetermined consistency expectations;
   c. through said human machine interface, selecting one or more of said presented scan data files for batch data processing in an order fixed by said human operator;
   d. under computer control, data processing each scan data file pursuant to the priority order established in said file selection step to produce a weld indications data file for each file data processed; and,
   e. after said data processing step, presenting a list of said processed weld indications data files to a human operator for review through said computer interface.

2. The method as recited in claim 1, further including the step prior to said selection step of excluding from being presented to said operator prior to said selection step any scan data files which fail said step of conducting a plurality of tests.

3. The method as recited in claim 2, wherein said step of presenting said processed weld indications data file in a list to a human operator further comprises the step of prioritizing said list in accordance with a computer programmed predetermined criteria.

4. The method as recited in claim 3, wherein said predetermined criteria comprises a file name parameter.

5. The method as recited in claim 4, wherein said step of conducting a plurality of tests further comprises the step of calculating an examination score associated with each tested scan data file resulting from said tests and wherein said score determines the priority order of each file being data processed.

6. The method as recited in claim 5, further including the step of using a selection engine to determine the priority of files to be data processed based upon computer programmed predetermined criteria.

7. The method as recited in claim 6, wherein said step of using a selection engine further comprises utilizing a rules set input into said selection engine to determine the priority of files to be data processed.

8. The method as recited in claim 6, wherein said step of using a selection engine further comprises utilizing a rules set input into said selection engine to determine the priority of files to be reviewed by said operator.

9. The method as recited in claim 1, wherein said data processing step comprises the steps of:
   a. wherein each said scan data file holds a plurality of two dimensional, coordinate based cell matrices representing slices of known thickness of a scanned weld seam, and wherein each cell holds a reflection amplitude value representing a potential weld flaw along the weld seam, using a computer processor to extract weld indications from said data file by saving all non-zero magnitude values in each said cell into a table recording weld indications while preserving location information of each said cell along said weld seam in said table;
   b. assigning a significance score to each said extracted indication saved in said new indications table based on a preselected criteria;
   c. ranking each said indication based upon said significance score and saving said ranking in said table;
   d. integrating said indications table into said scan data file; and,
   e. based on said significance score, electronically producing a human perceivable account showing a portion of said ranked indications along with associated location information for each in said weld seam for a weld inspector's review.

10. The method as recited in claim 9, wherein said step of presenting said processed weld indications data file in a list to a human operator further comprises the step of prioritizing said list in accordance with a computer programmed predetermined criteria.

11. The method as recited in claim 10, wherein said availability of a plurality of ultrasonic scan data files comprises a dynamically available set of scan data files held in computer storage continually receiving additional scan data files ready for data processing.

12. The method as recited in claim 11, wherein said step of conducting a plurality of tests further comprises the step of calculating an examination score associated with each tested scan data file resulting from said tests, and wherein said score determines the priority order of each file being data processed.

13. The method as recited in claim 12, wherein said computer storage comprises cloud-based computer storage.

14. A method for batch data processing of a plurality of ultrasonic scan data files, comprising the steps of:
   a. scanning a weld seam and storing a plurality of scan data files in computer data storage;
   b. testing each scan data file to determine if the data file is usable for extracting weld indications via a computer processor;
   c. for those data files that are usable for further data processing, producing a list of those usable files and presenting the list to a human operator via a computer display screen;
   d. said human operator selecting an order of data processing for said produced list of files via a human computer interface screen;
   e. responsive to said selected ordered list, data processing each scan data file in the order specified by the ordered list to produce a weld indications data table annotated into each scan data file; and,
   f. after said data processing step, presenting a list of said processed weld indications data files to a human operator for review.

15. The method as recited in claim 14, wherein said testing step further includes the steps of retrieving configuration values in each said scan data file to determine the existence of configuration inconsistencies in said data file based upon one or more predetermined consistency expectations to meet known industry compliance standards and excluding from being presented to said operator prior to said selection step any scan data files which fail said testing step.

16. The method as recited in claim 15, wherein said data processing step comprises the steps of:
   a. wherein each said scan data file holds a plurality of two dimensional, coordinate based cell matrices representing slices of known thickness of a scanned weld seam, and wherein each cell holds a reflection amplitude value representing a potential weld flaw along the weld seam, using a computer processor to extract weld indications from said data file by saving all non-zero magnitude values in each said cell into a table recording weld indications while preserving location information of each said cell along said weld seam in said table;
   b. assigning a significance score to each said extracted indication saved in said new indications table based on a preselected criteria;
   c. ranking each said indication based upon said significance score and saving said ranking in said table;
   d. integrating said indications table into said scan data file; and,
   e. based on said significance score, electronically producing a human perceivable account showing a portion of said ranked indications along with associated location information for each in said weld seam for a weld inspector's review.

17. The method as recited in claim 14, wherein said step of storing a plurality of scan data files comprises a dynamically receiving a stream of scan data files held in cloud-based computer storage which continually receives additional scan data files available for data processing.

18. The method as recited in claim 14, further including the step of using a selection engine to determine the priority of files to be data processed based upon computer programed predetermined criteria.

19. The method as recited in claim 18, wherein said step of using a selection engine further comprises utilizing a computer programed rules set input to determine said priority of files to be data processed and said priority of files to be reviewed by said examiner.

20. A method for batch data processing of a plurality of ultrasonic scan data files, comprising the steps of:
   a. a weld inspector accessing a computer screen interface listing a plurality of scan data files ready for extraction of weld indications via a data processing step;
   b. said weld inspector causing via said computer screen interface for each file in said listing to be processed for configuration data inconsistencies to determine if each file merits further data processing;

c. said weld inspector receiving via a computer interface screen a tested list of scan data files, said list excluding any files having data inconsistencies;
d. said weld inspector selecting via a human computer screen interface an order of data processing for said list of tested scan data files;
e. data processing each selected scan data file in the order selected by said weld inspector in order to extract meritorious weld indications held by each said scan data file; and,
f. producing a listing of all data processed files on a computer interface screen for said inspector to review, wherein said data processed listing orders said data processed files in an order determined by a computer programed predefined set of file constraints.

* * * * *